United States Patent [19]

Ishioka et al.

[11] 3,959,297

[45] May 25, 1976

[54] PROCESS FOR THE PREPARATION OF 3-CYANOPYRIDINE

[75] Inventors: Ryoji Ishioka, Tokyo; Norio Kametaka, Hiratsuka; Kuniomi Marumo, Tokyo, all of Japan

[73] Assignee: Showa Denko Kabushiki Kaisha, Tokyo, Japan

[22] Filed: Feb. 27, 1975

[21] Appl. No.: 553,627

[30] Foreign Application Priority Data

Mar. 14, 1974 Japan.............................. 49-28597
Jan. 13, 1975 Japan.............................. 50-5559

[52] U.S. Cl. ............................................. 260/294.9
[51] Int. Cl.$^2$........................................ C07D 213/57
[58] Field of Search ................................ 260/294.9

[56] References Cited
OTHER PUBLICATIONS
Kryukov, et al., Chem. Abstracts, Vol. 78(17), 110, 243-z, Apr. 30, 1973.

Oga, et al., Chem. Abstracts, Vol. 75(9), 63, 447v, Aug. 30, 1971.

*Primary Examiner*—Alan L. Rotman
*Attorney, Agent, or Firm*—Sherman & Shalloway

[57] ABSTRACT

A process for preparing 3-cyanopyridine by the ammoxidation of 2-methyl-5-ethylpyridine which comprises reacting 2-methyl-5-ethylpyridine with ammonia and oxygen in the vapor phase at an elevated temperature, using a specific catalyst consisting of a low-area carrier on which has been deposited vanadium oxide and other specific metal oxides, the reaction being carried out in the copresence of steam.

19 Claims, No Drawings

PROCESS FOR THE PREPARATION OF 3-CYANOPYRIDINE

This invention relates to a process for preparing 3-cyanopyridine (CP) continuously by the ammoxidation of 2-methyl-5-ethylpyridine (MEP).

CP is a compound valuable for use as the starting material for the synthesis of nicotinic acid and its amide which as a member of the vitamin B complex is useful in the fields of pharmaceuticals as well as additives for either food or feedstufs. That CP can be prepared by the ammoxidation of beta-picoline or MEP is known. In the method which uses beta-picoline as the starting material, the use of various catalysts consisting of the combinations of vanadium, chromium, molybdenum, titanium, tin, bismuth and phosphorus have been suggested in the prior art. Among these methods which use beta-picoline as the starting material there are some which provide CP in a considerably high yield, but these methods are unsuitable for commercial production for economic reasons, since the starting beta-picoline is relatively expensive. Hence, it is believed that the method using as the starting material MEP which can be obtained at a lower cost is of greater advantage. However, as MEP is a compound possessing the alkyl substituents in excess of that possessed by beta-picoline, there are such drawbacks as that on submission of MEP to the ammoxidation reaction, not only is there the formation of undesirable by-products, but also considerable difficulty is experienced in controlling the reaction. Again, the rate of production of the intended CP is extremely low. Thus, a satisfactory method of production of 3-cyanopyridine on a commercial scale has not been established as yet.

Heretofore, numerous catalysts, including vanadium oxide and the combinations of various metal oxides therewith, have been suggested, of which the metal oxide catalysts having vanadium and tin or vanadium and titanium as their active ingredients have been recognized as being especially effective. According to our findings, the selectivity for CP, the rate of production and the stability of the reaction are greatly influenced in the case of the ammoxidation of MEP by such factors as the class of the active catalyst ingredient used, the method of preparing the catalyst and the reaction conditions. For instance, even though the catalyst system consists of a combination of vanadium and tin or vanadium and titanium, which are hitherto known to be effective active catalyst ingredients, such undesirable by-products as 2,5-dicyanopyridine (DCP) or 5-ethyl-2-cyanopyridine are frequently formed in great amounts. When attempts are made to prepare either nicotinic acid or its amide from the reaction products containing such by-products, isocinchomeronic acid is formed from DCP, with the consequence that a decarboxylation step must be added to make the entire process extremely complicated. Further, difficulty is usually experienced in maintaining the ammoxidation reaction of MEP in a steady and stable state, and hence it frequently happens that the smooth progress of the reaction is impeded. For checking the formation of by-products and accomplishing the stabilization of the reaction, a method of maintaining the concentration of MEP of the starting gaseous mixture fed to the reaction system at a low value and concurrently feeding a large amount of steam has already been proposed and has been effective to a certain extent. However, in view of the fact that the concentration of MEP in the gas fed is exceedingly low and that the amount of steam admixed is considerably great as compared with the amount of MEP, not only the rate of production (space time yield g/l. cat. hr.) of CP is low, but also since the CP is recovered in a state in which it is diluted with a large amount of water, extra expenditure is required for its separation.

Suvorov of Soviet Union reports that CP could not be obtained but only DCP was obtained when the ammoxidation of MEP was carried out in the absence of steam using a catalyst obtained by compression molding into either tablet or granular form a powder mixture of vanadium pentoxide and titanium dioxide followed by calcination of the tablets or granules for 90 minutes at 900°C. (see Example 54 of British Pat. 1,317,064). On the other hand, he carried out an experiment of preparing CP by the ammoxidation of MEP using a catalyst of the same mixture of vanadium pentoxide and titanium dioxide molded into granular form, in the copresence of a large amount of steam, which experiment is reported in Soviet Union Patent 311,914. The results of this experiment, if summarized, are as follows:

| Example | (Rate of feed per l. of cat. hr.) | | | | MEP Concentration in feed gas (vol %) | $H_2O$/MEP mol ratio | Space Time yield of CP (g/l. cat.hr.) |
| --- | --- | --- | --- | --- | --- | --- | --- |
| | MEP (g) | Steam (g) | Air (l) | Ammonia (g) | | | |
| 1 | 17.5 | 870 | 2400 | 60 | 0.09 | 333.1 | 11.3 |
| 2 | 25.5 | 1100 | 4500 | 150 | 0.07 | 291 | 17.0 |
| 3 | 23.0 | 950 | 3000 | 75 | 0.10 | 278 | 16.7 |

To the best of our knowledge, the experimental results mentioned in the foregoing Soviet Union patent are most satisfactory of those that have been reported to date. However, as can be appreciated from the numerical values given above, the rate of feed of MEP and its concentration are exceedingly low while, on the other hand, the amount of steam that is admixed is very great as compared with that of the MEP. Hence, not only is the space time yield of the intended CP small, but it is also collected in a state where it is diluted with a great amount of water.

Thus, principally because of such hereinbefore-noted difficulties and inefficiencies as the formation of by-products, instability of the reaction, lowness of the space time yield of CP and that the CP is collected diluted with a large amount of water, the practice of the economic and commercial production of CP by the ammoxidation of MEP is being held back. As a consequence of our extensive research, we found that such factors as the choice of the active catalyst components to be used, the method of preparing the catalyst, the composition of the gas fed and the reaction conditions were of prime importance in carrying out this reaction effectively, and that these factors were mutually interrelated. It is therefore an object of this invention to provide a process for the preparation of CP by the ammoxidation of MEP that can be practiced commercially advantageously.

The process for preparing 3-cyanopyridine by the ammoxidation of 2-methyl-5-ethylpyridine of this invention consists in reacting 2-methyl-5-ethylpyridine with ammonia and oxygen at a temperature of 300° – 500°C. in the presence of a supported metal oxide catalyst as well as the copresence of steam. The metal oxide catalyst used is one obtained by depositing on a low-area carrier of a specific surface area of not more than 50 square meters per gram a combined two, three or four-component metal oxide selected from the vanadium-titanium, vanadium-zirconium, vanadium-titanium-zirconium, vanadium-titanium-tungsten, vanadium-zirconium-tungsten and vanadium-titanium-zirconium-tungsten combined metal oxides, followed by calcining the so treated mass at a temperature of 300° – 600°C. under a non-reducing atmosphere. The steam is used in an amount of 20 – 80 volume % based on the total volume of gas fed.

An important feature of the process of the invention resides in the use of this supported metal oxide catalyst that has been prepared by the foregoing special method. The catalyst carrier must be a low-area carrier whose specific surface area is not more than 50 square meters per gram. As regards low-area carriers, these are described in P. H. Emett, Catalysis, Vol. 1, p. 249 (Reinhold Publishing Co., New York, 1954), As specific examples of these low-area carriers, included are alpha-alumina (e.g. fused alumina), silicon carbide, mullite, fused zirconia, fused titania and burnt clay. All of these have specific surface areas less than 50 square meters per gram and are inert with respect to the ammoxidation reaction. Preferred is the use of alpha-alumina. Those having specific surface areas ranging from 30 to 0.01 square meters per gram are preferred. If a carrier is used whose specific surface area is so great as to exceed 50 square meters per gram, for example, active carbon, silica and aluminosilicate, difficulty is experienced in controlling the reaction on account of the heat evolved from the oxidation reaction of MEP being great, and there is the danger of a violent decomposition reaction taking place.

The supported metal oxide catalyst is formed by depositing the aforementioned combined two, three or four-component metal oxide on the foregoing low-area carrier and calcining the so treated mass at a temperature of 300° – 600°C. The several components that are deposited may be oxides or compounds that are converted to oxides on calcination. The deposition of the catalyst components uniformly on the carrier is conveniently carried out by using a compound which is soluble in either water or an aqueous solution of an inorganic or organic acid and impregnating the carrier with a solution of such a compound followed by drying the impregnated carrier. As compounds of this kind, mention can be made of the various oxyacid salts, oxysalts, oxides and hydroxides such, for example, as vanadium pentoxide, ammonium metavanadate, vanadyl citrate, vanadyl oxalate, titanium acetate, titanium hydroxide, zirconyl nitrate and ammonium paratungstate. As regards the weight ratios of the several components, usable are 0.05 – 10 atoms, and preferably 0.1 – 5 atoms, of titanium, zirconium or tungsten per atom of vanadium. The amount of vanadium component deposited based on the total weight of the supported catalyst should be 0.5 – 15% by weight, and preferably 1 – 7% by weight, calculated as oxide. The amount deposited of all the components of the catalyst should be up to about 30% by weight, and preferably 3 – 20% by weight, of the total catalyst weight. The calcination is carried out under a non-reducing atmosphere, it being convenient to carry out the calcination in atmospheric air. The calcination temperature must not exceed 600°C. and usually, a temperature ranging from 300° to 600°C, and preferably 400° – 550°C., is used. When the calcination temperature is less than 300°C., a metal oxide catalyst having the desired activity is not formed. On the other hand, if 600°C. is exceeded, there is an abrupt drop in the activity, and there takes place the formation of a large amount of DCP rather than the desired CP. The calcination time is usually about 3 – 10 hours, there being no special advantages in using a period longer than 10 hours for this purpose. Thus, the catalyst components are formed on the surface of the carrier as a mixed or composite oxide. The so obtained metal oxide catalyst exhibits a synergistic effect as a result of the cooperation of the several components. The components other than vanadium, i.e., titanium, zirconium and tungsten, each exhibit characteristic tendencies. Titanium exhibits a relatively high activity, while zirconium is effective in stabilizing the reaction. On the other hand, tungsten tends to widen the range of the optimum temperature of the reaction. When compared with the previously described two-component catalyst, the three or four-component catalyst ensures the stability of the reaction and, in addition, provides a higher yield of the CP. Thus, the latter catalyst is to be preferred.

The ammoxidation reaction of MEP according to the present invention is carried out using the above-described supported metal oxide catalyst and in the copresence of 20 – 80 volume % of steam based on the total volume of feed gas to the reaction system. The ammoxidation reaction per se, as is well known, consists in reacting MEP with ammonia and oxygen in the vapor phase at an elevated temperature, thereby accomplishing the oxidative ammonolysis of MEP. The gaseous mixture fed to the reaction system may contain such inert gases as nitrogen or carbon dioxide. Hence, the use of air as the source of oxygen is not only convenient but advantageous as well. In consequence of the use of the aforementioned specific supported metal oxide catalyst and the copresence of 20 – 80% by volume of steam, the process of this invention can be carried out at a concentration of 0.5 – 5% by volume, a much higher concentration of the MEP in the feed gas as compared with the conventional methods. As there is a tencency to a decline in the yield of CP formed when the concentration of MEP is raised, the conventional methods had to be carried out at a low concentration of the MEP. The $H_2O$/MEP mol ratio in this invention is about 30 – 160, and thus it can be seen that this value is also exceedingly small when compared with that of the hereinbefore-mentioned Soviet Union patent. Thus, the concentration of MEP in the gas fed is high and the amount of steam is small in the case of this invention, with the consequence that the cost for producing the steam is reduced. In addition, the separation and recovery of CP from the reaction product is facilitated. Hence, the invention process is exceedingly advantageous from the commercial standpoint. When the amount introduced of the steam is insufficient, the evolution of heat becomes great with the accompaniment of the burning of MEP and ammonia to cause a decline in the yield of the intended CP.

The oxygen is fed in an amount suitably of 4 – 30 mols, and preferably 5 – 15 mols, per mol of MEP. In the past, the oxygen was used in a great excess, but in this invention the amount is much less. This also is one factor making it possible to use the MEP in a high concentration. If the amount fed of the oxygen is less than 4 mols, the proportion of ethylcyanopyridine and DCP in the product formed increases and, on the other hand, if 30 mols is exceeded, there is a tendency to a decline in the yield of CP.

Ammonia is suitably fed in an amount of 5 – 100 mols, and preferably 10 – 80 mols, per mol of MEP. CP tends to be obtained in a higher yield in proportion as the amount of ammonia fed increases. However, special advantages are not obtained by feeding the ammonia in excess. On the other hand, when the amount of the ammonia fed is too small, the yield of CP declines.

The reaction is carried out at a temperature of 300° – 500°C., and preferably 320° – 470°C.

When air is used as the oxygen source in accordance with this invention, the space velocity of the feed gas to the reaction system, i.e., the gaseous feed mixture consisting of MEP, ammonia, air and steam, can be raised to a high velocity of, say, about 1500 – 10,000, l./l. cat. hr., and preferably 1800 – 8000 l./l. cat. hr. (the gas volume being calculated under standard conditions (0°C., 1 atm.)). Hence, the rate at which MEP is fed can be maintained at a high level of, say, about 50 – 200 g/l. cat. hr., and preferably 90 – 150 g/l. cat. hr. And the yield of CP in this case is usually about 60 – 75%, though differing somewhat depending upon the catalyst used and the reaction conditions. Thus, the CP can be obtained readily at a high space time yield of, say, about 50 – 130 g/l. cat. hr. Such a high space time yield was not possible of attainment by the conventional methods.

The principal effects and advantages of the process of the invention described hereinbefore can be summarized as follows:

a. The intended CP can be prepared in good yield and a remarkably high space time yield.

b. The reaction can be carried out stably and smoothly, there being formed little or no by-products.

c. The MEP concentration in the feed gas can be raised and the amount of steam can be reduced, with the consequence that the cost for producing steam can be reduced. In addition, the CP can be obtained as an aqueous solution of high concentration.

Thus, the present invention has established a process by which the preparation of CP by the ammoxidation of MEP can be carried out advantageously on a commercial scale.

One mode of practicing the invention process commercially comprises passing a gaseous feed mixture, while maintaining it at a prescribed temperature, through a supported catalyst layer packed in a multi-tube reactor rapidly cooling the reaction product gas leaving the reactor to condense the steam and dissolve the CP therein, separating the CP from said aqueous solution, and recycling the excess ammonia to the feed gas.

The following examples are given for more fully illustrating the invention.

EXAMPLE I-1

1.8 Grams of vanadium pentoxide was dissolved in a 30% aqueous oxalic acid solution, after which an aqueous solution of titanium acetate was added thereto in an atomic ratio of V:Ti of 1:0.5. To the so obtained aqueous solution was then added 36 grams of alpha-alumina of particle size 0.5 – 1.0 mm in diameter (specific surface area not greater than 1.0 square meter per gram) and evaporated to dryness on a hot water bath with frequent stirring. Next, the particles were calcined for 4 hours at 450°C. in an electric furnace in the presence of air to obtain a supported metal oxide catalyst.

Ten milliliters of the so obtained metal oxide catalyst was packed in a stainless steel reaction tube of 10 mm inside diameter, following which a gaseous mixture of the following composition was passed through the packed layer at a space velocity (SV) of 3800 l./l. cat. hr. (the gas volume being calculated under standard conditions) while maintaining the reaction temperature at 380°C.

|      | Vol. % | Mol ratio |
|------|--------|-----------|
| MEP  | 0.5    | 1         |
| $NH_3$ | 5.0    | 10        |
| Air  | 44.5   | 89        |
| $H_2O$ | 50     | 100       |

The foregoing reaction proceeded exceedingly stably and smoothly and, as a result, the conversion of MEP was 100%, the yield of CP based on the starting MEP was 58%, and the amount of by-product DCP formed was zero.

In the foregoing reaction the rate of feed of MEP corresponds to 102.6 g/l. cat. hr., and the space time yield (STY) of CP corresponds to 51.1 g/l. cat. hr.

EXAMPLES I-2 – I-9 AND CONTROL 1

Catalyst

In Examples I-2 – I-5 the same catalyst as that of Example I-1 was used. In Examples I-6 – I-9 catalyst prepared by varying the atomic ratio V:Ti as well as the calcination conditions were used. On the other hand, in Control 1 the catalyst used was one prepared by calcining at 650°C., a temperature without the scope of this invention. The particulars of these catalysts are shown in Table 1.

Reaction

The compositions of the feed gas and reaction conditions in these experiments and the results obtained are shown in Table 2.

Examples II-1 – II-7

Catalyst 1.8 Grams of vanadium pentoxide was added slowly to about 20 milliliters of a 30% aqueous oxalic acid solution and dissolved with heating. To the so obtained solution was added an oxalic acid solution of titanium hydroxide in an atomic ratio of V:Ti of a prescribed value. An alpha-alumina carrier was then added to the resulting combined solution to prepare a metal oxide catalyst in the same manner as in Example I-1. The foregoing oxalic acid solution of titanium hydroxide was prepared in the following manner. Aqueous solution of ammonia was added to an aqueous solution of titanium tetrachloride to precipitate titanium hydroxide, which was then separated by filtration and water-washed. The resulting wet, gel-like precipitate was then added to a 20% aqueous oxalic acid solution and dissolved with heating. The particulars of the catalysts used are shown in Table 1.

Reaction

The compositions of the feed gas and reaction conditions as well as the results obtained are shown in Table 2.

Examples III-1 – III-5

Catalyst

A solution of vanadium pentoxide in an aqueous oxalic acid solution and an aqueous zirconyl nitrate solution were mixed in an atomic ratio of V:Zr of a prescribed value, after which an alpha-alumina carrier was added to the combined solution to prepare by operating as in Example I-1 a metal oxide catalyst. The particulars of the catalyst used are shown in Table 1.

Reaction

The composition of the feed gas, the reaction conditions and the results obtained are shown in Table 2.

EXAMPLES IV-1 – VI-3 AND CONTROLS 2–3 a. 1.8 Grams of vanadium pentoxide was added to a 30% aqueous oxalic acid solution and dissolved with heating. (b) A gel-like precipitate of titanium hydroxide was prepared by adding 6 milliliters of 28% aqueous solution of ammonia to an aqueous solution containing 3.8 grams of titanium tetrachloride, following which the precipitate was washed with pure water and filtered by means of suction. The resulting gel in its as wet state was added to a 30% aqueous oxalic acid solution and dissolved with heating. (c) Ammonium paratungstate was dissolved in pure water with heating. These three solution were mixed in an atomic ratio of V:Ti:W of a prescribed value, following which 36 grams of alpha-alumina of particle size 0.5 – 1.0 mm in diameter (specific surface area not greater than 1.0 square meter per gram) was added followed by evaporating the particles to dryness on a hot water bath with suitable stirring. The particles were then calcined in an electric furnace for 3 hours at 450°C. in atmospheric air to obtain a supported metal oxide catalyst. The particulars of the catalysts used in the several experiments are shown in Table 1.

Ten milliliters of the above-described metal oxide catalyst was packed in a stainless steel reaction tube having an inside diameter of 10 mm, and the reaction was carried out by passing the gaseous mixture through the catalyst layer. The composition of the feed gas and the reaction conditions and also the results obtained are shown in Table 2.

Control 2 illustrates the instance of a reaction in which the amount of steam contained in the feed gas was without the scope of the present invention. Difficulty was experienced in controlling the reaction temperature, and the reaction was instable.

On the other hand, Control 3 illustrates the instance where the reaction was carried out using a catalyst prepared by calcination at 700°C., a calcination temperature without the scope of this invention.

EXAMPLES V-1 – V-7 AND CONTROL 4

A V-Ti-Zr three-component metal oxide catalyst was prepared by impregnating an alpha-alumina carrier with a combined aqueous solution consisting of an oxalic acid solution of vanadium pentoxide, an oxalic acid solution of titanium hydroxide and an aqueous solution of zirconyl nitrate followed by drying and calcination of the impregnated carrier. The atomic ratio of the three components and the calcination conditions are shown in Table 1.

The reaction was carried out as in Example IV. The compositions of feed gases and the reaction conditions of the several experiments and the results obtained are shown in Table 2.

Control 4 illustrates the instance where a non-supported metal oxide catalyst of a particle size 0.5 – 1.0 mm in diameter was used in carrying out the reaction, the catalyst being obtained by mixing in a ball mill vanadium pentoxide, titanium oxide and zirconium oxide, each of which were in powdered form, in an atomic ratio of 4:1:1, molding the mixture in tablet form, and thereafter calcining the tablets for 2 hours at 800°C. in an electric furnace.

EXAMPLE VI

A three-component metal oxide catalyst of V:Zr:W (atomic ratio of 1:0.8:0.2) was prepared by impregnating an alpha-alumina carrier with a combined aqueous solution consisting of an oxalic acid solution of vanadium pentoxide, an aqueous solution of zirconyl nitrate and an aqueous solution of ammonium paratungstate followed by drying and thereafter calcining the impregnated carrier for 3 hours at 450°C.

The particulars of the catalyst used in the reaction are shown in Table 1, while the composition of the feed gas, the reaction conditions and the results obtained are shown in Table 2.

EXAMPLES VII-1 – VII-4

An alpha-alumina carrier was impregnated with a combined aqueous solution consisting of an oxalic acid solution of vanadium pentoxide, an oxalic acid solution of titanium hydroxide, an aqueous solution of zirconyl nitrate and an aqueous solution of ammonium paratungstate, following which the impregnated carrier was dried and then calcined for 3 hours at 450°C. to prepare a V-Ti-Zr-W four-component metal oxide catalyst.

The particulars of the catalyst used in the reaction are shown in Table 1, while the composition of the feed gas, the reaction conditions and the results obtained are shown in Table 2.

Table 1

| Example No. | V | Atomic Ratio W | Ti | Zr | Calcination conditions | Amount deposited ($V_2O_5$, wt%) |
|---|---|---|---|---|---|---|
| I-1 | 1 | | 0.5 | | 450°C. 4 hr | 5 |
| 2 | 1 | | 0.5 | | ″ | ″ |
| 3 | 1 | | 0.5 | | ″ | ″ |
| 4 | 1 | | 0.5 | | ″ | ″ |
| 5 | 1 | | 0.5 | | ″ | ″ |
| 6 | 1 | | 1 | | ″ | ″ |
| 7 | 1 | | 1 | | ″ | ″ |

Table 1-continued

| Example No. | Atomic Ratio V | W | Ti | Zr | Calcination conditions | Amount deposited ($V_2O_5$, wt%) |
|---|---|---|---|---|---|---|
| 8 | 1 | | 1 | | 400°C. 4 hr | ″ |
| 9 | 1 | | 1 | | 500°C. 4 hr | ″ |
| Control 1 | 1 | | 1 | | 650°C. 4 hr | ″ |
| II-1 | 1 | | 1 | | 450°C. 4 hr | 2.5 |
| 2 | 1 | | 1 | | ″ | 5 |
| 3 | 1 | | 1 | | ″ | 7.5 |
| 4 | 1 | | 1 | | ″ | 5 |
| 5 | 1 | | 1 | | ″ | ″ |
| 6 | 1 | | 1 | | ″ | ″ |
| 7 | 1 | | 1 | | ″ | ″ |
| III-1 | 1 | | | 1 | 450°C. 4 hr | 5 |
| 2 | 1 | | | 1 | ″ | ″ |
| 3 | 1 | | | 1 | ″ | ″ |
| 4 | 1 | | | 1 | ″ | ″ |
| 5 | 1 | | | 0.5 | ″ | ″ |
| IV-1 | 1 | 0.2 | 1 | | 450°C. 3 hr | 5 |
| 2 | 1 | 0.2 | 1 | | ″ | ″ |
| 3 | 1 | 0.2 | 0.8 | | ″ | ″ |
| Control 2 | 1 | 0.2 | 1 | | ″ | ″ |
| Control 3 | 1 | 0.2 | 1 | | 700°C. 3 hr | ″ |
| V-1 | 1 | | 1 | 0.5 | 450°C. 3 hr | 5 |
| 2 | 1 | | 1 | 0.5 | ″ | ″ |
| 3 | 1 | | 1 | 0.5 | ″ | ″ |
| 4 | 1 | | 1 | 1 | ″ | ″ |
| 5 | 1 | | 1 | 1 | ″ | ″ |
| 6 | 1 | | 1 | 1 | ″ | ″ |
| 7 | 1 | | 1 | 1 | ″ | ″ |
| Control 4 | 4 | | 1 | 1 | 800°C. 2 hr | — |
| VI | 1 | 0.2 | | 0.8 | 450°C. 3 hr | 5 |
| VII-1 | 1 | 0.2 | 1 | 0.5 | 450°C. 3 hr | 5 |
| 2 | 1 | 0.2 | 1 | 0.5 | ″ | ″ |
| 3 | 1 | 0.2 | 1 | 0.5 | ″ | ″ |
| 4 | 1 | 0.2 | 1 | 0.5 | ″ | ″ |

Table 2

| Example No. | Composition of Feed gas (mol %) MEP | $NH_3$ | AIR | $H_2O$ | Mol ratio of components fed MEP | $NH_3$ | AIR | $H_2O$ | Amount fed of MEP (g/l.cat.hr) | Reaction condition S.V. | (°C) | CP (yield %) | DCP (yield %) | CP, STY (g/l.cat.hr) |
|---|---|---|---|---|---|---|---|---|---|---|---|---|---|---|
| I-1 | 0.5 | 5.0 | 44.5 | 50 | 1 | 10 | 89 | 100 | 102.6 | 3800 | 380 | 58 | 0 | 51.1 |
| 2 | 0.6 | 10.4 | 28 | 60 | 1 | 17.3 | 46.7 | 100 | 100.5 | 3100 | 370 | 61 | 0.5 | 52.7 |
| 3 | 0.9 | 15 | 40 | 44 | 1 | 16.7 | 44.4 | 48.9 | 107 | 2200 | 382 | 65 | 0 | 59.8 |
| 4 | 0.9 | 19 | 38 | 42 | 1 | 21.1 | 42.2 | 46.7 | 107 | 2200 | 385 | 64 | 1.5 | 58.9 |
| 5 | 1.0 | 17 | 31 | 51 | 1 | 17 | 31 | 51 | 97.2 | 1800 | 385 | 65 | 0 | 54.3 |
| 6 | 0.9 | 15 | 40 | 44 | 1 | 16.7 | 44.4 | 48.9 | 107 | 2200 | 360 | 64 | 0 | 58.9 |
| 7 | 0.8 | 13 | 34* | 38 | 1 | 16.3 | 42.5 | 47.5 | 103.7 | 2400 | 378 | 65 | 0 | 57.9 |
| 8 | 0.5 | 13 | 25 | 61.5 | 1 | 26 | 50 | 123 | 94.5 | 3500 | 370 | 70 | 0 | 56.9 |
| 9 | 0.5 | 13 | 25 | 61.5 | 1 | 26 | 50 | 123 | 94.5 | 3500 | 395 | 71 | 0 | 57.7 |
| Control 1 | 0.5 | 13 | 25 | 61.5 | 1 | 26 | 50 | 123 | 94.5 | 3500 | 445 | 42 | 15 | 34.1 |
| II-1 | 0.5 | 13 | 25 | 61.5 | 1 | 26 | 50 | 123 | 94.5 | 3500 | 400 | 71 | 1 | 57.7 |
| 2 | 0.5 | 13 | 25 | 61.5 | 1 | 26 | 50 | 123 | 94.5 | 3500 | 370 | 72 | 0 | 58.5 |
| 3 | 0.5 | 13 | 25 | 61.5 | 1 | 26 | 50 | 123 | 94.5 | 3500 | 365 | 70 | 0.5 | 56.9 |
| 4 | 0.4 | 10.5 | 40.1 | 49 | 1 | 26.3 | 100.3 | 122.5 | 92.9 | 4300 | 375 | 65 | 0 | 51.9 |
| 5 | 0.5 | 11.5 | 33.0 | 55 | 1 | 23 | 66 | 110 | 102.6 | 3800 | 380 | 69 | 0 | 60.8 |
| 6 | 0.6 | 14.0 | 19.4 | 66 | 1 | 23.3 | 32.4 | 110 | 103.7 | 3200 | 380 | 70 | 0 | 62.4 |
| 7 | 0.6 | 14.4 | 15.0 | 70 | 1 | 24 | 25 | 116.7 | 100.5 | 3100 | 385 | 66 | 0 | 57.0 |
| III-1 | 0.5 | 5 | 44.5 | 50 | 1 | 10 | 89 | 100 | 108 | 3800 | 420 | 53 | 0 | 49.2 |
| 2 | 0.6 | 10.4 | 28 | 60 | 1 | 17.3 | 46.7 | 100 | 106.5 | 3100 | 410 | 55 | 0 | 50.3 |
| 3 | 0.9 | 15 | 40 | 44 | 1 | 16.7 | 44.9 | 48.9 | 107 | 2200 | 415 | 61 | 0 | 56.1 |
| 4 | 0.7 | 17 | 33.3 | 49 | 1 | 24.3 | 47.6 | 70 | 98.3 | 2600 | 410 | 68 | 0 | 57.5 |
| 5 | 0.7 | 17 | 33.3 | 49 | 1 | 24.3 | 47.6 | 70 | 98.3 | 2600 | 410 | 67 | 0 | 56.6 |
| IV-1 | 0.5 | 18 | 24 | 58 | 1 | 36 | 48 | 116 | 99.9 | 3700 | 375 | 72 | 0 | 61.8 |
| 2 | 0.6 | 23 | 31 | 45 | 1 | 38.3 | 51.7 | 75 | 90.7 | 2800 | 375 | 71 | 0 | 55.3 |
| 3 | 0.5 | 18 | 24 | 58 | 1 | 36 | 48 | 116 | 99.9 | 3700 | 385 | 69 | 0 | 59.2 |
| Control 2 | 1.0 | 35 | 45 | 19 | 1 | 36 | 47 | 20 | 108.0 | 2000 | 385 | 23 | 14 | 21.4 |
| Control 3 | 0.5 | 18 | 24 | 58 | 1 | 36 | 48 | 116 | 99.9 | 3700 | 490 | 22 | 18 | 18.9 |
| V-1 | 0.6 | 28 | 29 | 43 | 1 | 46.7 | 48.3 | 71.7 | 145.8 | 4500 | 380 | 73 | 0 | 91.5 |
| 2 | 0.5 | 36 | 26 | 38 | 1 | 72 | 52 | 76 | 91.8 | 3400 | 385 | 75 | 0 | 59.2 |
| 3 | 0.6 | 23 | 31 | 45 | 1 | 38.2 | 51.7 | 75 | 90.7 | 2800 | 375 | 71 | 0 | 55.3 |
| 4 | 0.5 | 25 | 24 | 50 | 1 | 50 | 48 | 100 | 97.2 | 3600 | 384 | 74 | 0 | 61.8 |
| 5 | 0.6 | 30 | 28 | 42 | 1 | 50 | 46.7 | 70 | 97.2 | 3000 | 381 | 73 | 0.3 | 61.0 |
| 6 | 0.7 | 23 | 31 | 46 | 1 | 32.9 | 44.3 | 65.7 | 105.9 | 2800 | 371 | 71 | 0.3 | 64.6 |
| 7 | 0.7 | 26 | 22 | 51 | 1 | 37.1 | 31.4 | 72.9 | 94.5 | 2500 | 397 | 76 | 0 | 61.7 |
| Control 4 | 0.5 | 10 | 36 | 53 | 1 | 20 | 72 | 108 | 108.0 | 4000 | 430 | 51 | 13 | 47.3 |
| VI | 0.5 | 18 | 24 | 58 | 1 | 36 | 48 | 116 | 99.9 | 3700 | 395 | 68 | 0 | 58.4 |
| VII-1 | 0.5 | 17 | 22 | 61 | 1 | 34 | 44 | 122 | 105.3 | 3900 | 415 | 71 | 0 | 64.3 |
| 2 | 0.5 | 38 | 24 | 58 | 1 | 36 | 48 | 116 | 99.9 | 3700 | 415 | 71 | 0 | 61.0 |
| 3 | 0.6 | 23 | 31 | 45 | 1 | 38.3 | 51.7 | 75 | 90.7 | 2800 | 420 | 73 | 0 | 56.9 |

Table 2-continued

| Example No. | Composition of Feed gas (mol %) | | | | Mol ratio of components fed | | | | Amount fed of MEP (g/l.cat.hr) | Reaction condition | | Results of the reaction | | |
|---|---|---|---|---|---|---|---|---|---|---|---|---|---|---|
| | MEP | NH₃ | AIR | H₂O | MEP | NH₃ | AIR | H₂O | | S.V. | (°C) | CP (yield %) | DCP (yield %) | CP, STY (g/l.cat.hr) |
| 4 | 0.5 | 22 | 22 | 55 | 1 | 44 | 44 | 110 | 189.1 | 7000 | 440 | 69 | 0 | 112.1 |

*14 vol. % of N₂ fed additionally.

What we claim:

1. A process for preparing 3-cyanopyridine by the ammoxidation of 2-methyl-5-ethylpyridine which comprises reacting 2-methyl-5-ethylpyridine with ammonia and oxygen at a temperature of 300° – 500°C. in the presence of a supported metal oxide catalyst and the copresence of steam, said catalyst being one obtained by depositing on a low-area carrier of specific surface area of 0.01 – 50 square meters per gram a combined two to four-component metal oxide selected from the group consisting of the vanadium-zirconium, vanadium-titanium-zirconium, vanadium-titanium-tungsten, vanadium-zirconium-tungsten and vanadium-titanium-zirconium-tungsten combined metal oxides, and calcining the metal oxide-deposited carrier at a temperature of 300 – 600°C. under a nonreducing atmosphere, said steam being used in an amount of 20 – 80 volume % based on the total volume of the feed gas to the reaction system.

2. The process of claim 1 wherein said low-area carrier is one having a specific surface area of 0.01 – 30 square meters per gram.

3. The process of claim 1 wherein the calcination temperature is 400°– 550°C.

4. The process of claim 1 wherein said supported metal oxide catalyst is a catalyst deposited with the three or four components.

5. The process of claim 1 wherein the content of 2-methyl-5-ethylpyridine in the feed gas is 0.5 – 5 volume % based on the total volume of the feed gas.

6. The process of claim 1 wherein the mole ratio of steam to 2-methyl-5-ethylpyridine in the feed gas is about 30 – 160.

7. The process of claim 1 wherein the mole ratio of ammonia to 2-methyl-5-ethylpyridine in the feed gas is about 5 – 100.

8. The process of claim 1 wherein the mole ratio of oxygen to 2-methyl-5-ethylpyridine in the feed gas is about 4 – 30.

9. The process of claim 1 which comprises using air as the oxygen source.

10. The process of claim 9 wherein the space velocity of the feed gas is about 1500 – 10,000 l./l. cat. hr (the gas volume being calculated under standard conditions).

11. The process of claim 1 wherein the reaction temperature is 320° – 470°C.

12. The process of claim 1 wherein said low-area carrier is selected from the group consisting of alpha-alumina, silicon carbide, mullite, fused zirconia, fused titania and burnt clay.

13. The process of claim 1 wherein the weight ratio of the titanium, zirconium or tungsten in the combined metal oxides is from 0.05–10 atoms per atom of vanadium, the amount of vanadium component deposited based on the total weight of the supported catalyst is 0.5–15% by weight calculated as oxide, and the total amount of the metal components deposited on the catalyst is up to about 30% by weight, based on the total catalyst weight.

14. The process of claim 1 wherein the weight ratio of the titanium, zirconium or tungsten in the combined metal oxides is from 0.1–5 atoms per atom of vanadium, the amount of vanadium component deposited based on the total weight of the supported catalyst is 1–7% by weight calculated as oxide, and the total amount of the metal components deposited on the catalyst is up to about 3–20% by weight, based on the total catalyst weight.

15. The process of claim 1 wherein the metal oxide deposited on the low-area carrier is vanadium-zirconium combined metal oxide.

16. The process of claim 1 wherein the metal oxide deposited on the low-area carrier is vanadium-titanium-zirconium combined metal oxide.

17. The process of claim 1 wherein the metal oxide deposited on the low-area carrier is vanadium-titanium-tungsten combined metal oxide.

18. The process of claim 1 wherein the metal oxide deposited on the low-area carrier is vanadium-zirconium-tungsten combined metal oxide.

19. The process of claim 1 wherein the metal oxide deposited on the low-area carrier is vanadium-titanium-zirconium-tungsten combined metal oxide.

* * * * *